United States Patent [19]

Konrad et al.

[11] Patent Number: 5,273,638

[45] Date of Patent: Dec. 28, 1993

[54] NUCLEOTIDE SEQUENCE DETERMINATION EMPLOYING MATCHED DIDEOXYNUCLEOTIDE TERMINATOR CONCENTRATIONS

[75] Inventors: Kenneth D. Konrad, Long Beach; Stephen L. Pentoney, Jr., Yorba Linda, both of Calif.

[73] Assignee: Beckman Instruments, Inc., Fullerton, Calif.

[21] Appl. No.: 769,422

[22] Filed: Sep. 30, 1991

[51] Int. Cl.$^5$ .................. G01N 27/26; G01N 27/447
[52] U.S. Cl. ............................ 204/299 R; 204/180.1; 204/182.8
[58] Field of Search ........................................ 204/299

[56] References Cited

U.S. PATENT DOCUMENTS

| | | | |
|---|---|---|---|
| 3,576,727 | 4/1971 | Evatt | 204/299 R |
| 4,284,491 | 8/1981 | Vesterberg | 204/299 R |
| 4,729,947 | 3/1988 | Middendorf et al. | 435/6 |
| 4,830,830 | 5/1989 | Tamotu et al. | 204/299 R X |
| 4,863,849 | 9/1989 | Melamede | 435/6 |
| 4,891,120 | 1/1990 | Setti et al. | 204/299 R |
| 5,045,172 | 9/1991 | Guzman | 204/299 R |

FOREIGN PATENT DOCUMENTS

| | | |
|---|---|---|
| 0351138 | 1/1990 | European Pat. Off. |
| 2155176A | 9/1985 | United Kingdom |

OTHER PUBLICATIONS

Konrad, K. D., Pentoney, S. L., "Process for Optimizing Nucleotide Sequence Determination", U.S. Patent application Ser. No. 07/768,491 filed Sep. 30, 1991.

Sanger, F. et al, "DNA Sequencing with chain-terminating inhibitors"; Proc. Natl Acad. Sci. USA; vol. 74, No. 12, pp. 5463-5467, Dec. 1977.

Toneguzzo, F., et al; "Use of a Chemically Modified T7 DNA Polymerase for Manual and Automated Sequencing of Supercoiled DNA"; Research Report; Bio Techniques; vol. 6, No. 5, pp. 460-469, (1988).

Kambara, Hideki, et al; "Optimization of Parameters in a DNA Sequenator Using Fluorescence Detection"; Bio/Technology; vol. 6, pp. 816-821, Jul. 1988.

Smith, Lloyd M., et al; "Fluorescence Detection in Automated DNA Sequence Analysis"; Nature; vol. 321, Jun. 12, 1986.

(List continued on next page.)

Primary Examiner—Donald R. Valentine
Assistant Examiner—John S. Starsiak, Jr.
Attorney, Agent, or Firm—William H. May; P. R. Harder; Wen Liu

[57] ABSTRACT

A method of positively deciphering a DNA sequence of a sample by comparing data of two electropherograms obtained from separate electrophoresis of products from two complete sequence reactions of the same sample, whereby dideoxynucleotide terminators of different but matched concentration ratios are employed for the two reactions. The sequencing chemistry is chosen to result in terminator-concentration dependent in peak intensity in the electropherograms. By appropriately choosing the matched concentration ratios of the terminators used in the two sequence reactions, ambiguities in the discrimination of the peaks in the result of one sequence reaction can be resolved by comparing the result of the other sequence reaction. The sequence of the sample can therefore be deciphered to a high degree of accuracy. For fluorescence detection of electrophoresis of the sequence reactions, three ddNTP terminators and one fluor are included in the sequencing chemistry of each reaction. The position of the fourth terminator in the sequence is determined from the location of the gaps or tiny peaks in the background signal in the electropherogram which appear between the peaks produced by the three ddNTP terminators used. A dual channel electrophoresis device facilitates obtaining two matched electropherograms of two simultaneous sequence reactions which employ matched concentration ratios of ddNTP terminators. The device comprises a single radiation source and two parallel electrophoresis channels simultaneously operating under substantially similar conditions.

16 Claims, 3 Drawing Sheets

OTHER PUBLICATIONS

Prober, James M., et al; "A System for Rapid DNA Sequencing with Fluorescent Chain-Terminating Dideoxynucleotides"; Research Articles, Science, vol. 238, pp. 336–341.

Tabor, Stanley, et al; "DNA Sequence Analysis With a Modified Bacteriophage T7 DNA Polymerase"; The Journal of Biological Chemistry; vol. 265, No. 14, pp. 8322–8328, May 15, 1990.

Ansorge, W., et al; "One Label, One Tube, Sanger DNA Sequencing in One and Two Lanes on a Gel"; Nucleic Acids Research, vol. 18, No. 11, pp. 3419–3420, submitted Apr. 24, 1990.

Ansorge, W., et al; "Automated Sanger DNA sequencing with one label in less than four lanes on gel"; Journal of Biochemical and Biophysical Methods, pp. 47–52, (1989).

Drossman, Howard; "High-Speed Separations of DNA Sequencing Reactions by Capillary Electrophoresis"; Anal. Chem., 1990, pp. 900–903.

Swerdlow, Harold, et al; "Capillary gel electrophoresis for rapid, high resolution DNA sequencing"; Nucleic Acids Research, vol. 18, No. 6, Feb. 20, 1990, pp. 1415–1419.

Abstract No. TL 105; Second International Symposium on "HPCE"; Jan. 29–31, 1990.

Guttman, A., et al; "Analytical and Micropreparative Ultrahigh Resolution of Oligonucleotides by Polyacrylamide Gel High-Performance Capillary Electrophoresis"; Anal. Chem., 1990, 62, pp. 137–141.

Zagursky, Robert J., et al; "DNA Sequencing Separations in Capillary Gels on a Modified Commercial DNA Sequencing Instrument"; Bio Techniques; vol. 9, No. 1 (1990), pp. 74–78.

Tabor, Stanley, et al; "Effect of manganese ions on the incorporation of dideoxynucleotides by bacteriophage T7 DNA polymerase and *Escherichia coli* DNA polymerase l"; Proc. Natl. Acad. Sci. USA, vol. 86, pp. 4076–4080, Jun. 1989.

Kambara, Hideki, et al; "Real Time Automated Simultaneous Double-Stranded DNA Sequencing Using Two-Color Fluorophore Labeling"; Bio/Technology; vol. 9, pp. 648–651; Jul. 1991.

CAS Bio Tech Updates-DNA Formation & Repair, Issue 16, Abstract No. 1352, 1990.

Oken, Donald E.; "Quantitation of Picogram Quantities of Serum Albumin by Ultramicrodisc Electrophoresis and Direct Densitometry"; Microchemical Journal 15, pp. 557–563 (1970).

Sambrook, J. et al; A Laboratory Manual, 2nd edition, "Molecular Cloning"; cover page copyright page and pp. 13.3–13.10.

NUCLEOTIDE SEQUENCE DETERMINATION EMPLOYING MATCHED DIDEOXYNUCLEOTIDE TERMINATOR CONCENTRATIONS

INTRODUCTION

1. Field of the Invention

The present invention relates to DNA sequencing and more particularly relates to determination of DNA sequence by electrophoresis.

2. Background of DNA Sequencing

One of several rapid DNA sequencing techniques in current use is the so called chain termination method introduced by Sanger et al. [1]. The method basically involves enzymatically generating separate populations of radioactively or fluorescence labeled oligonucleotides that begin from a fixed point and terminate randomly at a fixed residue or combination of residues by the presence of a dideoxynucleotide ("ddNTP"). Because every base in the DNA has an equal chance of being the variable terminus, each population consists of a mixture of oligonucleotides whose length are determined by the location of a particular base along the length of the original DNA. These populations of oligonucleotides are then resolved by electrophoresis under conditions that can discriminate between individual DNAs that differ in length by as little as one nucleotide.

DNA sequencing techniques currently practiced relative to gel slab electrophoresis are three variations of the Sanger et al. chain termination method. A single fluorescence or radioactively labeled primer can be elongated in four separate reactions each with a different ddNTP and the products separated electrophoretically in four lanes in a gel slab [1,2,3]. Alternatively, four separate reactions each employing a different ddNTP can be performed with primers labeled with four different fluorophores (of different colors), the reactions combined, and the products separated in one lane in a gel slab [4]. A third approach utilizes four ddNTPs, each labeled with a different fluorophore, in one reaction which is also analyzed in one lane in a gel slab [5]. The detection of the fluorescence or radioactivity of the labeled oligonucleotides separated by electrophoresis provides an indication of the relative position of the oligonucleotides in the DNA sequence.

Both four-fluor approaches are advantageous in maximizing the number of reactions which may be analyzed per gel, however both have disadvantages as well. The different excitation and emission characteristics of the four fluorophores necessitates the use of complicated and expensive hardware and ultimately limits the system sensitivity. In addition the different fluorophores can differentially alter the electrophoretic mobility of the reaction products which necessitates sophisticated software correction to decipher the DNA sequence.

Tabor and Richardson have recently shown that incorporation of $Mn^{++}$ into sequencing buffers using T7 DNA polymerase nearly eliminates template sequence dependent variability in ddNTP utilization [6]. They have exploited this observation in a protocol using a single fluorescence-labeled primer and different concentrations of the four ddNTP's in which sequence is determined based on peak intensity in a single slab-gel lane.

Ansorge et. al. have also described a similar strategy [7]. Using this approach the advantages of single-lane sequencing are realized without the disadvantages associated with the use of four different fluors. Ansorge et al. [8] published that in principle, it is possible to determine the sequence with one-dye in only one lane on the gel by choosing the proper ddNTP ratios for all bases, carrying out reactions in one tube and applying the product in one lane. Ansorge however recognized that the error rate in this one-lane method (10% or even more) is too high at the time of publication. This is believed to be at least partially due to the inability to utilize a broad enough range of concentrations to allow discrimination between four dideoxynucleotides (i.e. limited dynamic range). It is noted that too high a concentration of dideoxynucleotides will reduce the amount of sequence information by terminating reactions too close to the primer.

DNA sequencing based upon slab gel electrophoresis techniques has a low throughput. Capillary gel electrophoresis overcomes many of the inherent drawbacks of slab gel electrophoresis and potentially offers high throughput. Typically the result of electrophoresis of a DNA reaction mixture is represented by an electropherogram. Using the Tabor and Richardson one-dye approach with different terminator concentrations, the DNA sequence is called by analyzing the relative peak heights in the electropherogram (i.e. ideally four peak height categories when four ddNTPs are used in different concentrations), each peak ideally corresponding to the presence of oligonucleotides of a particular length and which have been terminated by a ddNTP. However one often encounters difficulties in discrimination of the peaks in the electropherogram.

Difficulties in peak discrimination are manifested by poor resolution of the relative peak heights, peak compression, missing peaks, detection errors, etc. When analyzing relative peak heights, it is often times difficult to determine which height category a particular peak falls into when attempting to call the corresponding base. Peak heights corresponding to a particular ddNTP can vary by 20% or more. Thus when concentrations of two ddNTPs are not sufficiently different, ambiguity arises when identifying two peaks within normal peak height variations. Also, it is often times difficult to distinguish small peaks from background signals Peak compression arises because of the formation of secondary (and unwanted) structures through intramolecular base pairing and the sequencing fragments containing such secondary structures can display increased electrophoretic mobility and "compression artifacts". In other words, fragments of different lengths can co-migrate in the same zone to result in the same peak in the electropherogram, or a peak with a "shoulder" (a small partial peak very close to the side of a peak).

Sometimes, there may be "gaps" between peaks at places where peaks are expected to be present. This may be caused by detection error or the sequencing reaction. In such a situation, one cannot confirm what the corresponding nucleotides are in the sequence.

It would be desirable for one to be able to discriminate with assurance the sequence from the electropherogram.

SUMMARY OF THE INVENTION

The present invention is directed to a method of determination of a DNA sequence of a sample by comparing data of two electropherograms obtained from separate electrophoresis of products from two complete sequence reactions of the same sample, whereby dideoxynucleotide ("ddNTP") terminators of different but matched concentration ratios are employed for the two reactions. Since the size of a peak in the electropherogram corresponding to a nucleotide in the sequence is dependent on the concentration of the associated terminator, the nucleotide is identified by looking at the peak size relative to those nearby corresponding to the other terminators. By appropriately choosing the matched concentration ratios of the terminators used in the two sequence reactions, ambiguities in the discrimination of the peaks in one sequence reaction can be resolved by comparing with the result of the other sequence reaction The sequence of the sample can therefore be deciphered to a high degree of accuracy.

In the described embodiment, for fluorescence detection of electrophoresis of the sequence reactions, three ddNTP terminators and one fluor are included in the sequencing chemistry of each reaction. The position of the fourth terminator in the sequence is determined from the presence of gaps or tiny peaks in the electropherogram which appear between the peaks produced by the three ddNTP terminators used.

A dual channel electrophoresis device is disclosed which facilitates obtaining two matched electropherograms of two simultaneous sequence reactions which employ matched concentration ratios of ddNTP terminators. The device comprises a single radiation source and two parallel electrophoresis channels simultaneously operating under substantially similar conditions.

DESCRIPTION OF THE ILLUSTRATED EMBODIMENTS

The following description is of the best presently contemplated mode of carrying out the invention. This description is made for the purpose of illustrating the general principles of the invention and should not be taken in a limiting sense. The scope of the invention is best determined by reference to the appended claims.

While the present invention is described hereinbelow in reference to fluorescence detection in capillary electrophoresis, it is however understood that the present invention is not limited to such implementation but is applicable to other types of detection schemes and slab gel electrophoresis.

The implementation of capillary electrophoresis for DNA sequence analysis is well known in the art and its theory will not be described herein. The potential of high performance capillary electrophoresis for the separation of DNA fragments generated enzymatically using the ddNTP chain terminator approach has recently been demonstrated by Drossman et al [9], Swerdlow and Gesteland [10], and by Cohen et al [11]. These authors have all demonstrated three main points. First, they have demonstrated that capillary electrophoresis, using polyacrylamide gel-filled capillaries is capable of sufficiently resolving sequencing fragments, at least in the size range 20 to 750 bases. Second, they have demonstrated that laser induced fluorescence detection provides sufficient sensitivity to detect the presence of labeled DNA fragments (generated over this size range) present within the narrow confines of the capillary separation channel. Finally, the authors have demonstrated that these sequencing mixtures can indeed be separated much faster by capillary electrophoresis than by conventional slab-gel electrophoresis.

Figure 1:
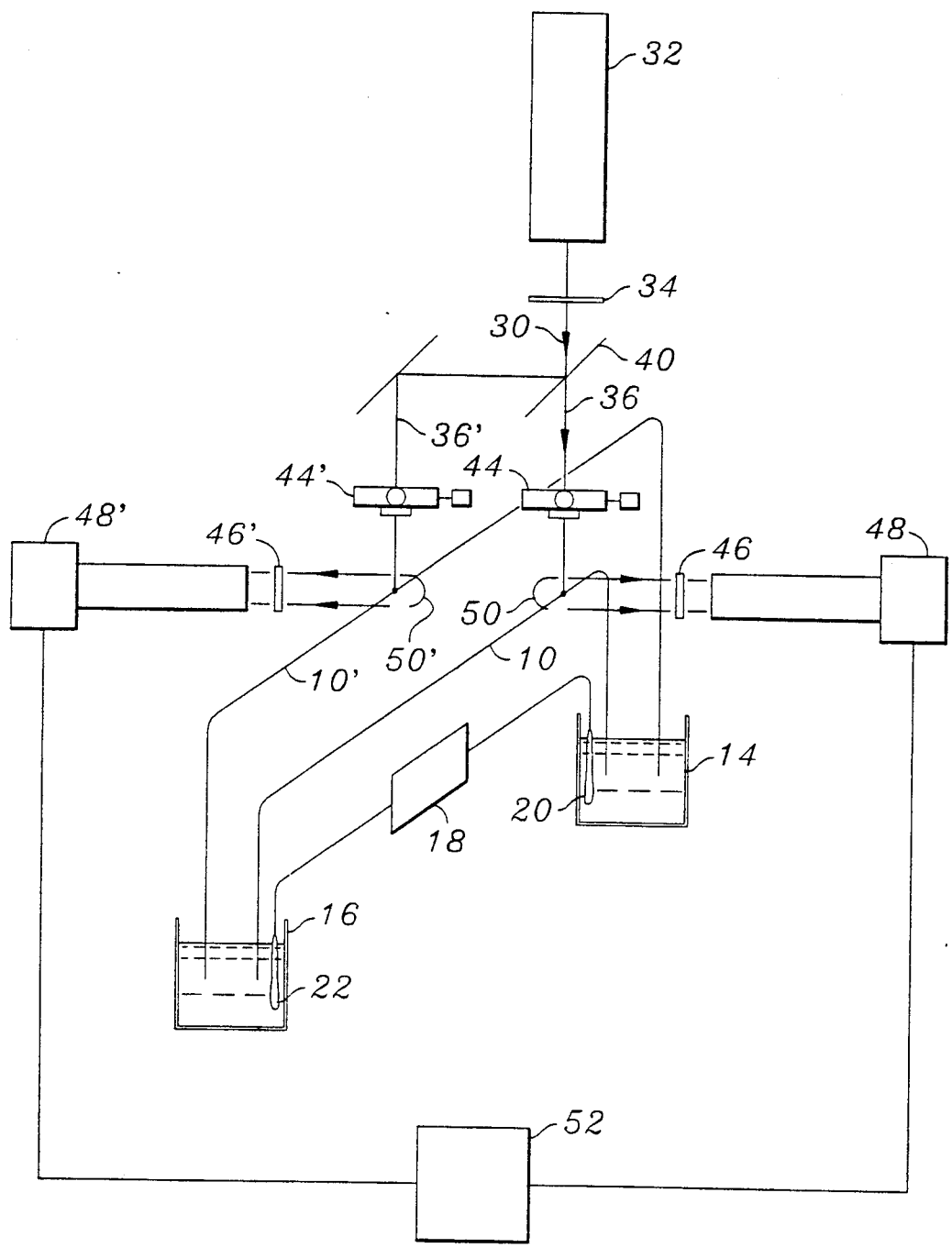
FIG. 1 is a schematic illustration of a dual channel capillary electrophoresis device in accordance with one embodiment of the present invention.

The instrumentation for carrying out electrophoresis for obtaining "matched" sequence data will be set forth first. It is noted that the term "matched" as used herein relates to coexistence of results of complete sequence reactions in which each reaction is capable of indicating all four possible nucleotides (despite the fact that only three ddNTP terminators are used in the example set forth herein). A schematic of the instrument is illustrated in FIG. 1. There are two electrophoresis channels in the instrument, each defined by a fused silica capillary column (10, 10') (less than 500 μm i.d.) and associated detection hardware. In each channel, the two ends of a capillary column (10, 10') are submerged in electrolyte 12 contained in reservoirs 14 and 16. A high voltage power supply 18 capable of applying a high electric field (typically 10–30 KV) is electrically connected to the electrolyte 12 in the reservoirs 14 and 16 using electrodes 20 and 22. The capillary column (10, 10') is filled with a separation support medium which may be an electrolyte solution, gel electrolyte or other suitable conductive medium. In the example given below, the separation support medium used is gel. Prior to electrophoresis, the sample (in this case the product from the sequence reaction) to be electrophoretically separated is electrokinetically injected into one end of the capillary column (10, 10'). With the two ends of the capillary column (10, 10') dipped into the electrolyte, the high voltage power supply 18 is turned on to cause electrophoresis of the DNA sample which results in separation into its ddNTP terminated fragments.

The particular illustrated detection technique in FIG. 1 is laser induced fluorescence. Reference is made to U.S. Pat. No. 4,675,300 to Zare et al for a more detailed description of the principle of this detection technique. The beam 30 from a laser source 32 (such as a "green" Helium-Neon laser) is filtered using filter 34 and split into two beams 36 and 36' of substantially equal intensity by a beam splitter 40. For each channel, the split beam (36, 36') is focused using lens (44, 44') onto a section of the capillary column (10, 10'). The DNA sample being separated by electrophoresis have been labelled with fluorescent dye prior to electrophoresis. This will be explained in detail below. The laser beam (36, 36') causes fluorescence of the dye thereby giving an indication of the presence of the labelled nucleotide passing the laser irradiated section of the capillary column (10, 10'). The fluorescence is filtered by band-pass filter (46, 46') and detected by use of a photomultiplier tube (48, 48'). To increase sensitivity of the detection, the fluorescence emanating from the capillary column is collected and collimated using a paraboloid reflector (50, 50'), and directed to the photomultiplier tubes (48, 48') The laser irradiated section of the capillary column (10, 10') is positioned at the focal point of the paraboloid reflector (50, 50'). The output from the photomultiplier tubes 48 and 48' are directed to a data acquisition device 52 which may include a computer which outputs the results of electrophoresis as electropherograms.

Electrophoresis is carried out using gel filled capillary columns as they provide good separation resolution of DNA fragments. The gel column is adapted from that described in U.S. patent application No. 7/688,182 which is commonly assigned to the assignee of the present invention and is incorporated by reference herein. The gel used is a "linear" matrix polymerized without cross-linkers Gels of other formulations may be used.

The present instrument for carrying out simultaneous electrophoresis of two sequencing reaction mixtures is preferred over consecutive electrophoresis of the mixtures. The present instrument provides substantially the same operating conditions (e.g. voltage, temperature buffer concentration, source radiation, background noise, etc.) for both reactions so that the results of the electrophoresis can be compared without additional considerations of otherwise different electrophoresis conditions.

DNA sequencing reactions were modified from a protocol which was obtained from U.S. Biochemicals. One $\mu$g of M13mp18 DNA was mixed with 0.5 picomole of primer and 2 $\mu$L of 5× reaction buffer (Sequenase TM kit) in a total volume of 10 $\mu$L. This was heated to 65° C., allowed to cool to 37° C., and 1 $\mu$L of 0.1M DTT solution and 1 $\mu$L of $Mn^{++}$ buffer (Sequenase TM kit) were then added. 9 $\mu$L of a prewarmed termination mix were then added, followed by 2 $\mu$L of undiluted Sequenase TM. The termination mix was prepared by mixing 4.0 $\mu$L, 1.7 $\mu$L, and 0.7 $\mu$L of mixtures, respectively containing ddATP, ddGTP and ddCTP terminators. Thus the terminators are present in the concentration ratio 4A:1.7G:0.7C:0T The matched termination mix was prepared by mixing 4.0 $\mu$L, 1.7 $\mu$L, and 0.7 $\mu$L of mixtures, respectively containing ddCTP, ddTTP, ddGTP terminators. Thus in the matched mixture, the terminators are present in the concentration 4C:1.7T:0.7G:0A. The determination of the optimum matched concentration ratio is disclosed in a copending patent application Ser. No. 07/768,491 entitled "Process for Optimizing nucleotide sequence determination" by the same inventors and commonly assigned to the assignee of the present invention, which is herein incorporated by reference.

Each reaction was incubated for 30 minutes at 37° C. after which it was placed on ice and 2.0 $\mu$L of 3.0M sodium acetate were added followed by 60 $\mu$L of ice-cold ethanol. The DNA was pelleted by centrifugation at 12,000 RPM for 15 minutes and rinsed once with 70% ethanol. The pellet was then dried and resuspended in 2.0 $\mu$L of 80% formamide, 10 mM EDTA. The sample was heated to 95° C. for 1 minute just prior to injection onto the capillary.

Figure 2:
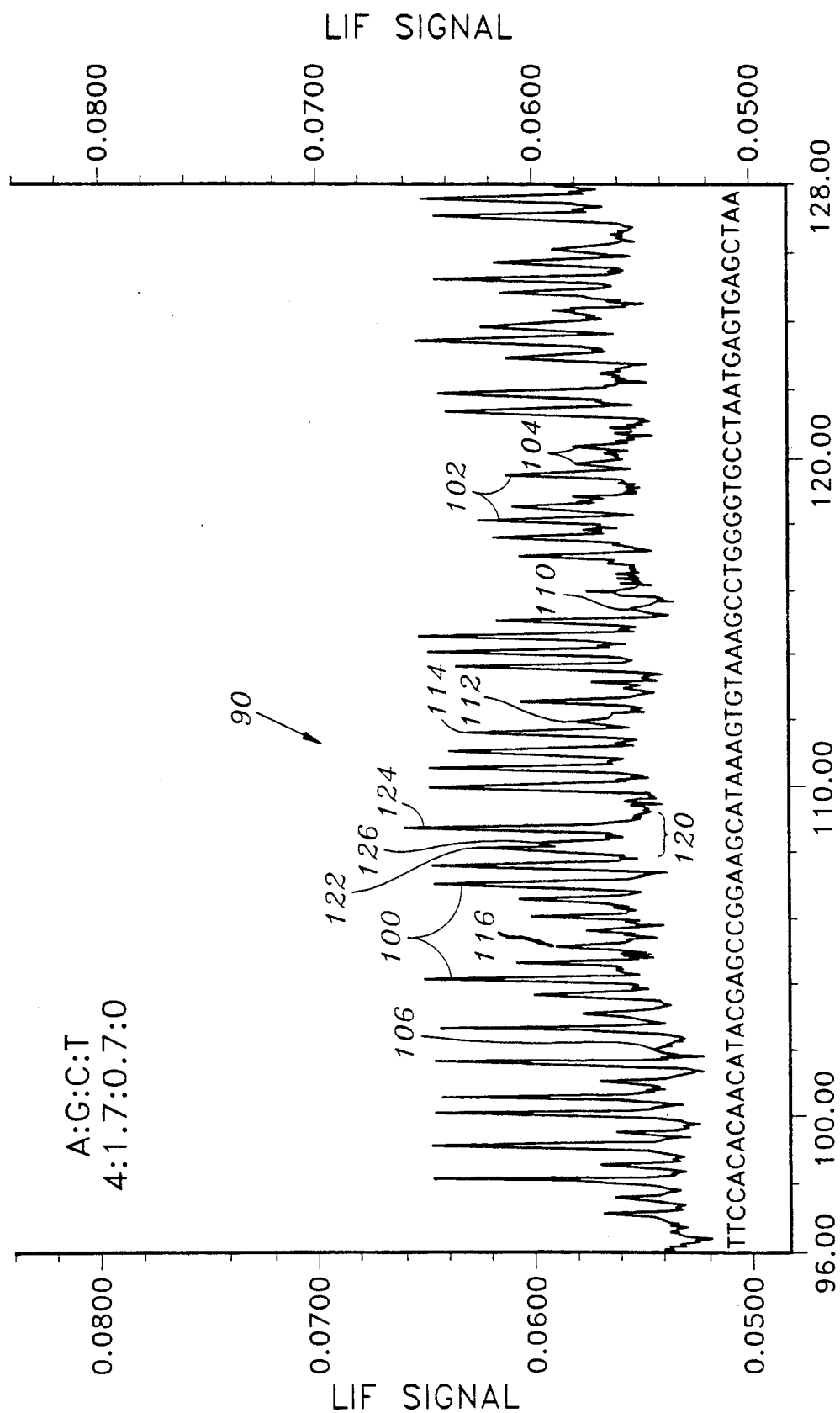
FIG. 2 is an electropherogram obtained from electrophoresis of a sequence reaction using three terminators of a particular concentration ratio.
Figure 3:
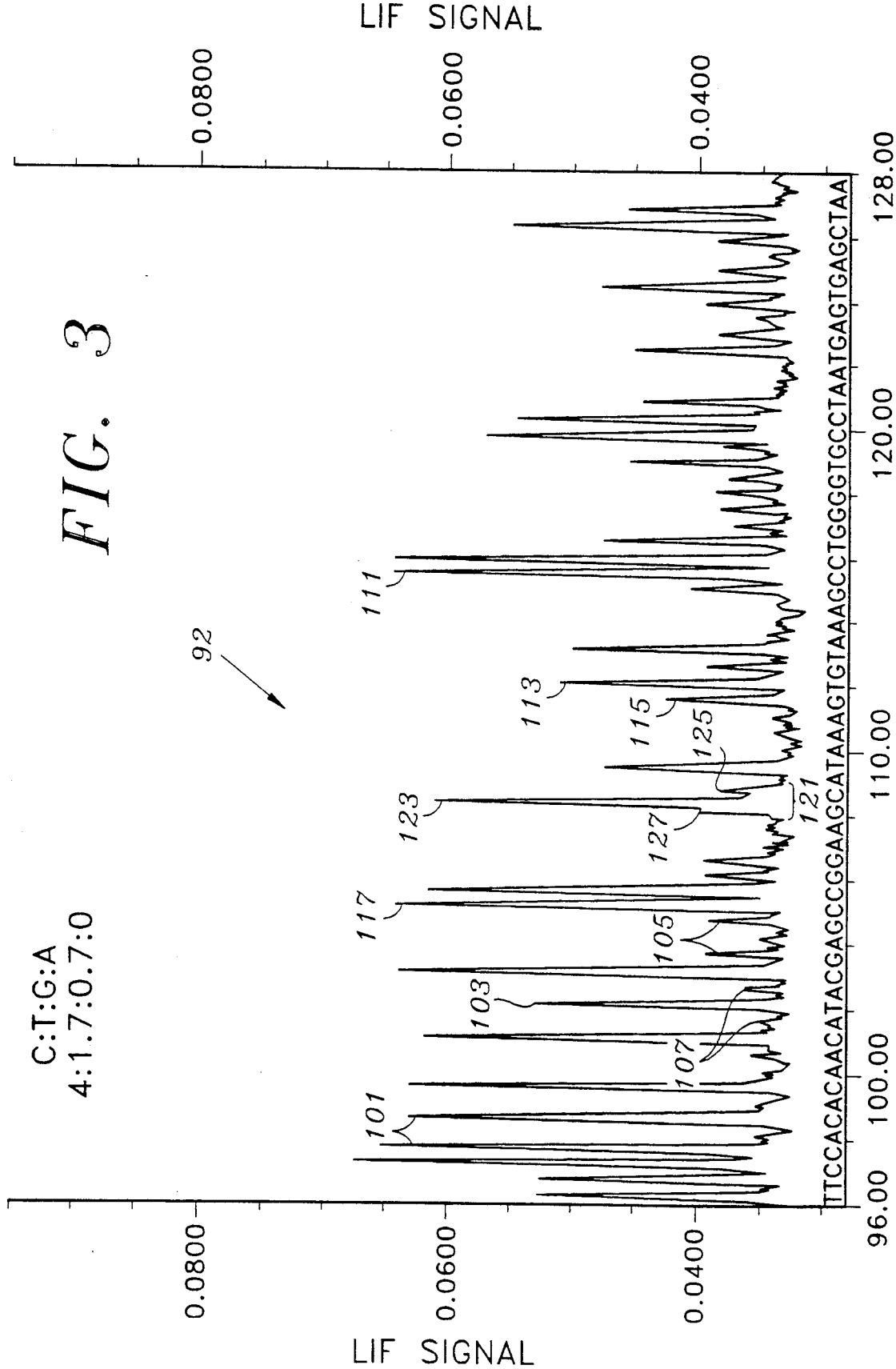
FIG. 3 is an electropherogram obtained from electrophoresis of a sequence reaction using three terminators of a matched concentration ratio.

FIGS. 2 and 3 show the electropherograms 90 and 92 obtained from the electrophoresis of the two matched reaction mixtures. In each electropherogram, there are a series of peaks each representing the presence of an oligonucleotide of increasing base length having a ddNTP terminator (the shorter oligomers reaching the detection section sooner than the longer bases). Each electropherogram contains result of complete sequence reactions, each indicating four types of nucleotides "A", "C", "T", and "G". There are generally four size groups of peaks: large, (e.g. peaks 100 and 101), medium (e.g. peaks 102 and 103), small (e.g. peaks 104 and 105), and tiny peaks mixed in background signals (e.g. peaks 106 and 107). It has been demonstrated by Tabor and Richardson the sequence dependent variation in peak size can be reduced by including $Mn^{++}$ in the terminator mixture [6]. Thus, in the absence of reaction dependent peak variations, the peak size in the electropherogram is proportional to the concentration of the corresponding ddNTP terminator and the fluorescence thereof. One can therefore identify the particular ddNTP by discriminating between the peak sizes. The relatively largest size peaks 100 and 101 correspond to the highest concentration terminator; the medium size peaks 102 and 103 correspond to the medium concentration terminator; the small size peaks 104 and 105 correspond to the least concentration terminator; and the tiny peaks 106 and 107 correspond to no terminator or a terminator with negligible concentration.

A drawback of the Tabor and Richardson approach has been that the amount of readable sequence is limited by the ability to detect and discern sequencing products terminated by the least concentrated ddNTP. In accordance with the present invention, it was possible to read sequence from reaction mixtures generated using only three of four possible ddNTP terminators in each reaction. This is possible because the "gaps" or tiny peaks (due to premature termination) may be assigned to the fourth base. This is very advantageous in that it allows the least concentrated ddNTP to be a larger proportion of the reaction mixture, thus making better use of the dynamic range of detection. For example, in a four-ddNTP mix having concentration ratio 8:4:2:1, the least concentrated ddNTP is present at 1 part in 15. While in a 4:2:1 three-ddNTP mix, the least concentrated ddNTp is present at 1 part in 7. According to the present two reaction approach, the representation (concentration) of the ddNTP's is reversed (high concentration to low and vice versa) in each reaction, and the identity of the gaps in one reaction is confirmed by the presence of the largest peaks in the other. Using only three ddNTPs should allow sufficient use of the system dynamic range to discriminate among the peak identities at concentrations which will not compromise sequence information. In fact, the pool of extendable reaction products should last longer with only three terminators, allowing more sequence to be determined per unit of primer. Notwithstanding the fact that the full benefit of the present invention would not be realized by employing four terminators in each of the matched reactions, it is however understood that the present invention does not exclude such an approach.

Specifically, with respect to the electropherogram 90 in FIG. 2, the relatively large peaks 100 represent the presence of oligonucleotides having ddATP terminators in the sequence. The medium size peaks 102 represent the presence of oligonucleotides having ddGTP terminators in the sequence. The small size peaks 104 represent the presence of oligonucleotides having ddCTP terminators in the sequence. In the absence of ddTTP terminators, oligonucleotides terminating with T-nucleotides are not expected to be present in the sequence although they appear as tiny peaks 106 within the background signal between neighboring peaks.

With respect to the electropherogram 93 in FIG. 3, the relatively large peaks 101 represent the presence of ddCTP terminators in the sequence. The medium size peaks 103 represent the presence of ddTTP terminators in the sequence. The small size peaks 105 represent ddGTP terminators in the sequence. In the absence of ddATP terminators, oligonucleotides terminating with A-nucleotides are not expected to be present in the sequence although they appear as tiny peak 107 within the background signal between neighboring peaks.

Because of background signal and the difficulty in determining the baseline in the electropherograms 90 and 92, it is often difficult to discriminate the small peaks from the tiny peaks or the background signal. For example, peak 110 in FIG. 2 is ambiguous between a "C" and "T" determination. In order to be able to confirm that a small peak is not a background signal or tiny peak, or vice versa, the two electropherograms 90 and 92 are compared. Since the terminators are employed in different concentration ratios in obtaining the two electropherograms, and further that the concentration ratios are selected in a matched manner, any true background signal will remain as background signal and a true peak will have a different size in the second electropherogram. Accordingly, if peak 110 is indeed a "C", the counterpart peak 111 in FIG. 3 is expected to be of large size, which turned out to be so in this case. If the peak 111 turns out to be of medium size in FIG. 3, then one would conclude that the peak 111 is a "T". An example of a "T" that looks like a "C" in the electropherogram 90 is peak 112 in FIG. 2. The "T" determination is confirmed by comparing to the electropherogram 92 in FIG. 3 which shows a counterpart peak 113 of relative medium size. This removes any ambiguity between small peaks and tiny peaks or background signal. As a rule of thumb, generally for each terminator, the difference in concentrations for each terminator for the two reactions should preferably be maintained as large as possible to allow maximum contrast for positive discrimination by comparing the two electropherograms.

It has been found that the peaks corresponding to adjacent concentrations in the relative concentration ratio of ddNTPs (i.e. immediate higher or lower concentration) are often times difficult to discriminate. For example in FIG. 2, it is difficult to determine whether peak 114 is a "G" or "A", and whether peak 116 is a "C" or "G". It is thus recommended that any two terminators of adjacent concentrations in the first reaction should preferably be assigned non-adjacent concentrations in the second reaction to maximize contrast with the peaks in the first reaction. In the given example, the A:G:C:T concentration ratio in the first reaction is given a C:T:G:A concentration ratio. It is unavoidable for the ddATP and ddGTP terminators to be adjacent in both reactions but the high contrast of ddATP terminators in the two reactions (highest and zero concentrations in the two reactions relative to the other terminators) offsets for this.

By comparing electropherograms 90 and 92 in FIG. 2 and 3, one can confirm that peak 114 is a "G" and peak 116 is a "C" as evident by peak sizes of the counterpart peaks 115 and 117 in FIG. 3.

It is noted in FIG. 2 there is compression of peaks in the region 120 which appears to show two peaks 122 and 124, apparently a "G" and an "A", and possibly a third peak (a "shoulder") 126. However, looking at the counterpart region 121 in FIG. 3, there appears to be two peaks 123 and 125 which appears to be "C" and "A", and again a third peak (a shoulder) 127. The comparison of the two regions allow one to conclude that there are actual three peaks compressed into two peaks coupled with the shoulder peak and they should represent the sequence "GCA". Shoulder peak 126 is determined to be a "C" and shoulder peak 127 is determined to be a "G" by deduction from the comparison of the electropherograms 90 and 92.

The actual sequence determined from the two electropherograms 90 and 92 is indicated at the base of each electropherogram in FIG. 2 and 3.

In summary, simultaneous separation of two matched mixtures will improve the accuracy of sequence discrimination in the following ways. (1) Each channel contains complete sequence information on all four possible types of nucleotides A, C, G and T. (2) The data in each channel is compared with the other in order to help resolve ambiguous peak identification originating either from mistakes made by the polymerase during one of the sequencing reactions or difficulty in discrimination caused by the terminator concentration ratio in a single channel. The comparison of two such reactions results in a more robust sequence determination.

The combination of a single fluor sequencing chemistry and the high speed, high resolution separations afforded by high performance capillary electrophoresis promises the ability to automate DNA sequence determination relatively inexpensively. Although the described embodiment conducts simultaneous electrophoresis, the basic concept of using terminator mixtures of matched concentration ratios can be applied also to running sequencing reactions twice in a sequential manner.

It should be possible to utilize two spectrally different dyes and multiplex (superimpose) the matched sequencing reactions in a single electrophoresis run, using a single capillary. Signals from the fluorescence of the dyes can be separated and respectively can be used to construct two matched electropherograms. However, the use of a single fluor and two separate columns rather than a single column and two different fluors has two primary advantages. (1) Better signal to noise is expected in the system using two columns because a greater quantity of each sample may be loaded onto the column. (2) The laser induced fluorescence detection system is cheaper due to single laser requirement.

The electropherogram peak analysis can be performed using computers. The software for such analysis are within the skill of the art and will not be discussed here. Basically, the software would filter out noise and background and identify the peaks and their relative sizes in each electropherogram. The results of two matched electropherograms will be compared to confirm the particular terminating ddNTP represented by the peaks.

It is noted that the electropherograms sometimes do not start from the same reference base due to variation between the initial migration at the start of the two electrophoresis runs. The offset however can be easily removed in the data reduction process. Once the general sequence is identified from the electropherograms, the peaks can be aligned accordingly to allow comparison.

While the invention has been described with respect to the illustrated embodiments in accordance therewith, it will be apparent to those skilled in the art that various modifications and improvements may be made without departing from the scope and spirit of the invention. Accordingly, it is to be understood that the invention is not to be limited by the specific illustrated embodiments, but only by the scope of the appended claims.

REFERENCES

The following references are incorporated by reference herein:

1. Sanger, F.; Nicklen, S.; Coulson, A. R. *Proc. Natl. Acad. Sci. U.S.A.*, 74/5463-5467 (1977).
2. Toneguzzo, F.; Glynn, S.; Levi, E.; Mjolsness, S.; Hayday, A., *BioTechniques*, 6/460-469, (1988).
3. Kambara, H.; Nishikawa, T.; Katayama, Y.; Yamagichi, T., *Biotechnology*, 6/816-821, (1988).
4. Smith, L. M.; Sanders, J. Z.; Kaiser, R. J.; Hughes, P.; Dodd, C.; Connell, C. R.; Heiner, C.; Kent, S. B. H.; Hood, L. E., *Nature*, 321/674-679, (1986).
5. Prober, J. M.; Trainor, G. L.; Dam, R. J.; Hobbs, F. W.; Robertson, C. W.; Zagursky, R. J.; Cocuzza, A. J.; Jenson, M. A.; Bowmeister, K., *Science*, 238/336-341, (1987).
6. Tabor, S.; Richardson, C. C., *J. Biol. Chem.*, 265/8322-8328, (1990).
7. Ansorge, W.; Zimmermann, J.; Schwager, C.; Stegemann, J.; Erfle, H.; Voss, H., *Nuc. Ac. Res.*, 18/3419-3420, (1990).
8. Ansorge W.; Voss H.; Wirkner U.; Schwager C.; Stegemann, J.; Pepperkok R.; Zimmermann J.; Erfle H., *J. Biochemical and Biophsical Methods*, 20/47-42 (1989).
9. Drossman, Howard; Luckey, John A.; Kostichka, Anthony J.; Smith, Lloyd M., Paper TL107, *Second International Symposium on High Performance Capillary Electrophoresis*, San Francisco, Calif., January (1990). Drossman, Howard; Luckey, John A.; Kostichka, Anthony J.; D'Cunha, Jonathan; Smith, Lloyd, M., *Anal. Chem.*, 62/900-903, (1990).
10. Swerdlow, Harold; Gesteland, Raymond, *Nucleic Acids Research*, 18/#6/1415-1419, (1990).
11. Cohen, A. S.; Najarian, D.; Gilbert, T. R.; Kager, B. L.; Abstract TL105, *Second International Symposium on High Performance Capillary Electrophoresis*, San Francisco, Calif., January, (1990).
12. Guttman, A.; Cohen, A. S.; Heiger, D. N.; Karger, B. L., *Anal. Chem.*, 62/137-141, (1990).

We claim:
1. An apparatus for performing capillary electrophoresis of two samples comprising:
   a first separation capillary column containing a first sample to be separated into its components;
   a second separation capillary column containing a second sample to be separated into its components;
   means for causing separation by electrophoresis of the first and second samples simultaneously;
   radiation means for irradiating detection points along the first and second capillary columns; and
   detection means for individually detecting radiation corresponding to separated first sample in the first capillary column and separated second sample in the second capillary column.

2. An apparatus as in claim 1 wherein the means for causing separation comprises a same buffer source for both first and second capillary columns.

3. An apparatus as in claim 2 wherein the means for causing separation further comprises a same voltage source for both first and second capillary columns.

4. An apparatus as in claim 1 wherein the first and second samples are DNA sequence mixtures which are obtained by performing first and second sequencing reactions on a sample DNA having an unknown DNA sequence, each using at least three ddNTPs from a group of four ddNTPs W, X, Y, and Z; wherein for the first sequencing reaction, three ddNTPs X, Y and Z are selected from the group of four ddNTPs, the first sequencing reaction producing a first sequence mixture; wherein for the second sequence reaction, three ddNTPs W, Y and Z are selected, the second sequencing reaction producing a second sequence mixture; wherein the apparatus further comprises:
   means for obtaining a first set of data peaks each representing the presence of ddNTP terminated oligonucleotides of a particular size in the first sequence mixture passing through the detection point in the first capillary column, the relative sizes of the data peaks being dependent on the concentration of the respective ddNTP;
   means for obtaining a second set of data peaks representing the presence of ddNTP terminated oligonucleotides of a particular size in the second sequence mixture passing through the detection point in the second capillary column, the relative sizes of the data peaks being dependent on the concentration of the respective ddNTP;
   means for comparing the first and second sets of data peaks to determine the DNA sequence of the sample DNA, whereby possible missing or ambiguous data peaks in one set of data peaks is resolved by referring to the second set of data peaks.

5. An apparatus as in claim 1 wherein the first and second capillary columns have an internal diameter of less than 500 $\mu$m.

6. An apparatus as in claim 1 wherein the detection means outputs first and second data sets representing the components of the first and second samples, respectively.

7. An apparatus as in claim 6 further comprising means for comparing the first and second data sets in a manner to determine the components of the first and second samples.

8. An apparatus as in claim 7 wherein the first and second samples has substantially the same components which have been processed by first and second processes to render different detection results such that the first and second data sets are different, and wherein the means for comparing determines the components of the same first and second samples by cross-referencing the first and second data sets.

9. An apparatus as in claim 1 wherein the radiation means includes a same radiation source for detection operatively coupled to both the first and second capillary columns.

10. An apparatus for performing capillary electrophoresis of two samples comprising:
    a first separation capillary column containing a first sample to be separated;
    a second separation capillary column containing a second sample to be separated;
    means for causing separation by electrophoresis of the first and second sample simultaneously; and
    a same radiation source for detection operatively coupled to both the first and second capillary columns.

11. An apparatus for determining DNA sequence of a sample DNA by performing capillary electrophoresis on first and second sequence mixtures which are obtained by performing first and second sequencing reactions on the sample DNA, each using at least three ddNTPs from a group of four ddNTPs W, X, Y, and Z; wherein for the first sequencing reaction, three ddNTPs X, Y and Z are selected from the group of four ddNTPs, the first sequencing reaction producing a first sequence mixture; wherein for the second sequence reaction, three ddNTPs W, Y and Z are selected, the second sequencing reaction producing a second sequence mixture; the apparatus comprising:

a first separation capillary column containing the first sequence mixture to be separated into its components;

a second separation capillary column containing the second sequence mixture to be separated into its components;

means for causing separation by electrophoresis of the first and second sequence mixtures simultaneously;

radiation means for irradiating first and second detection points along the first and second capillary columns, respectively;

detection means for individually detecting radiation corresponding to separated first sequence mixture in the first capillary column and separated second sequence mixture in the second capillary column;

means for obtaining a first set of data peaks each representing the presence of ddNTP terminated oligonucleotides in the first sequence mixture of a particular size passing through the first detection point in the first column, the relative sizes of the data peaks being dependent on the concentration of the respective ddNTP;

means for obtaining a second set of data peaks representing the presence of ddNTP terminated oligonucleotides of a particular size in the second sequence mixture passing through the second detection point in the second capillary column, the relative sizes of the data peaks being dependent on the concentration of the respective ddNTP.

12. An apparatus as in claim 11 further comprising means for comparing the first and second sets of data peaks to determine the sequence of the sample DNA, whereby possible missing or ambiguous data peaks in one set of data peaks is resolved by referring to the second set of data peaks.

13. An apparatus as in claim 12 wherein the means for causing separation comprises a same buffer source for both first and second capillary columns.

14. An apparatus as in claim 13 wherein the means for causing separation further comprises a same voltage source for both first and second capillary columns.

15. An apparatus as in claim 11 wherein the radiation means includes a same radiation source for detection operatively coupled to both the first and second capillary columns.

16. An apparatus as in claim 15 wherein the radiation source is a laser for laser induced fluorescence of the separated oligonucleotides.

* * * * *